United States Patent
Brown et al.

(10) Patent No.: US 7,356,112 B2
(45) Date of Patent: Apr. 8, 2008

(54) COMPUTED TOMOGRAPHY SCANNING

(75) Inventors: Kevin John Brown, Horsham (GB); David Jaffray, Etobicoke (CA); Jeffrey H. Siewerdsen, Toronto (CA); Marcel van Herk, Amsterdam (NL); Jan-Jakob Sonke, Amsterdam (NL)

(73) Assignee: Elekta AB (Pub), Stockholm (SE)

( * ) Notice: Subject to any disclaimer, the term of this patent is extended or adjusted under 35 U.S.C. 154(b) by 0 days.

(21) Appl. No.: 11/531,471

(22) Filed: Sep. 13, 2006

(65) Prior Publication Data
US 2007/0025496 A1   Feb. 1, 2007

Related U.S. Application Data

(63) Continuation of application No. 10/760,627, filed on Jan. 20, 2004, now abandoned.

(30) Foreign Application Priority Data

Jan. 21, 2003 (GB) ................................. 0301278.8
Nov. 28, 2003 (GB) ................................. 0327675.5

(51) Int. Cl.
*G21N 23/083* (2006.01)
(52) U.S. Cl. ................................. 378/8; 378/19; 378/65
(58) Field of Classification Search .................... 378/8, 378/19, 65
See application file for complete search history.

(56) References Cited

U.S. PATENT DOCUMENTS

| | | | |
|---|---|---|---|
| 5,271,055 A * | 12/1993 | Hsieh et al. | 378/95 |
| 6,353,653 B1 * | 3/2002 | Edic | 378/8 |
| 6,385,286 B1 * | 5/2002 | Fitchard et al. | 378/65 |
| 6,385,288 B1 * | 5/2002 | Kanematsu | 378/65 |
| 6,434,215 B1 * | 8/2002 | Cesmeli | 378/8 |
| 6,480,560 B2 * | 11/2002 | Hsieh | 378/8 |
| 6,535,570 B2 * | 3/2003 | Stergiopoulos et al. | 378/8 |
| 6,721,386 B2 * | 4/2004 | Bulkes et al. | 378/8 |
| 6,792,066 B1 * | 9/2004 | Harder et al. | 378/4 |
| 6,865,248 B1 * | 3/2005 | Rasche et al. | 378/8 |
| 6,865,254 B2 * | 3/2005 | Nafstadius | 378/65 |
| 6,898,456 B2 * | 5/2005 | Erbel | 600/428 |
| 6,937,696 B1 * | 8/2005 | Mostafavi | 378/95 |
| 2004/0081269 A1 * | 4/2004 | Pan et al. | 378/4 |

* cited by examiner

*Primary Examiner*—Edward J. Glick
*Assistant Examiner*—Thomas R. Artman
(74) *Attorney, Agent, or Firm*—Bromberg & Sunstein LLP

(57) ABSTRACT

Artifacts in the reconstructed volume data of cone beam CT systems can be removed by the application of respiration correlation techniques to the acquired projection images. To achieve this, the phase of the patients breathing is monitored while acquiring projection images continuously. On completion of the acquisition, projection images that have comparable breathing phases can be selected from the complete set, and these are used to reconstruct the volume data using similar techniques to those of conventional CT. Any phase can be selected and therefore the effect of breathing can be studied. It is also possible to use a feature in the projection images such as the patient's diaphragm to determine the breathing phase. This feature in the projection images can be used to control delivery of therapeutic radiation dependent on the patient's breathing cycle, to ensure that the tumor is in the correct position when the radiation is delivered.

10 Claims, 3 Drawing Sheets

COMPUTED TOMOGRAPHY SCANNING

The present application is a continuation application of U.S. patent application Ser. No. 10/760,627, filed Jan. 20, 2004, now abandoned which in turn claimed priority from United Kingdom Patent Application 0327675.5, filed Nov. 28, 2003, and from United Kingdom Patent Application 0301278.8, filed Jan. 21, 2003; each of which is hereby incorporated by reference.

FIELD OF THE INVENTION

The present invention relates to scanning by computed tomography (CT).

BACKGROUND ART

CT scanning is a process for imaging the internal structure of a patient. In conventional CT scanning, a beam of x-rays is projected through the patient and its attenuation is measured. At the same time, the apparatus is rotated about an axis passing longitudinally through the patient. Thus, data is acquired as to the attenuation of the beam in each direction in the plane in which rotation takes place. From this data, the internal structure of the patient on that plane can be computed. The patient or apparatus is then indexed along the axis and a further plane (known as a 'slice') is then investigated. A three dimensional image of the patient can then be constructed from the various slices. One problem is that over the time required to acquire the necessary slices, the patient is not motionless. Gross motor movement can be avoided by suitable instruction to the patient, but even so each slice is acquired at a different phase of the breathing cycle. This results in a beating artifact due to the different frequency of breathing and slice acquisition.

Two ways have been used to solve this problem. On is to trigger the CT on a particular phase of the patients breathing. This is termed 'respiration gated CT' and implies that one CT slice is acquired for every breath. This means that it takes a long time to acquire a complete volume of data.

Another technique is to monitor the phase of the patients breathing whilst acquiring CT slices continuously. Once the data is acquired, slices that have comparable breathing phase are selected from the complete set and these are then used to visualize the volume. This has the advantage that any phase can be selected retrospectively and therefore the effect of breathing can be studied. This is termed 'respiration correlated CT'.

Conventional CT scans have the disadvantage that the resolution along the axis is poor since it corresponds to the slice thickness. It is theoretically straightforward to increase this, but doing so results in a correspondingly longer acquisition time, or the need to rotate the apparatus correspondingly faster. Both options also give rise to an attendant reduction in contrast in the measured beam. Accordingly, 'cone beam CT' methods have been developed, in which a conical beam of radiation is directed at the patient and a two-dimensional image acquired via a flat panel detector. This apparatus is then rotated around the patient axis and a three-dimensional image is reconstructed from the set of two-dimensional images. As the individual slices are eliminated, there is the same resolution in all directions of the image. Likewise, as there are no slices the above-mentioned breathing artifact is absent since there can be no variation in patient position between slices.

SUMMARY OF THE INVENTION

We have however found that there are other artifacts in the reconstructed volume data of cone beam CT systems, which we have traced to patient breathing movements. In addition, the motion is not measurable in the reconstructed volume data. This can be a particular problem in cone beam systems due to the long time required for acquisition, typically 1-2 minutes.

The techniques used in conventional CT scanners cannot be used directly in a cone beam system as the data is acquired in 2D projection images, and therefore slices cannot be selected from the resulting data. However, respiration correlation techniques could be applied to the acquired projection images rather than the reconstructed CT volume. To achieve this, we propose monitoring the phase of the patients breathing while acquiring projection images continuously. On completion of the acquisition, projection images that have comparable breathing phases can be selected from the complete set, and these are used to reconstruct the volume data using similar techniques to those of conventional CT. An advantage is that any phase can be selected and therefore the effect of breathing can be studied.

Breath control systems are available, intended for use in conventional CT scanning, and which could be used to monitor the patient's breathing. As an alternative, however, it is possible to use a feature in the projection image(s) to determine the breathing phase. A suitable feature is the position of the patient's diaphragm. This can then be used to select the relevant images to be used in the projection process.

It is known in the field of convention CT scanning to be advantageous to prompt the patient visually and audibly in order to ensure a regular amplitude and pattern of breathing. Techniques such as these could usefully be applied in the present invention. Furthermore this feature in the projection images can be used to control delivery of therapeutic radiation dependent on the patient's breathing cycle, to ensure that the tumour is in the correct position when the radiation is delivered. This will provide a direct measure of the patient's breathing phase, a significant improvement as compared to current methods that use external markers affixed to the patient. The use of a 3D volume data set generated using the same patient position and contemporaneous with the treatment will remove significant uncertainties.

The present invention further provides a radiotherapy device comprising a respiration correlated cone beam CT scanner and a source of therapeutic radiation, in which therapeutic radiation is delivered during the scan at times correlated with the patient's breathing cycle.

BRIEF DESCRIPTION OF THE DRAWINGS

An embodiment of the present invention will now be described by way of example, with reference to the accompanying figures in which.

DETAILED DESCRIPTION OF SPECIFIC EMBODIMENTS

Figure 1:
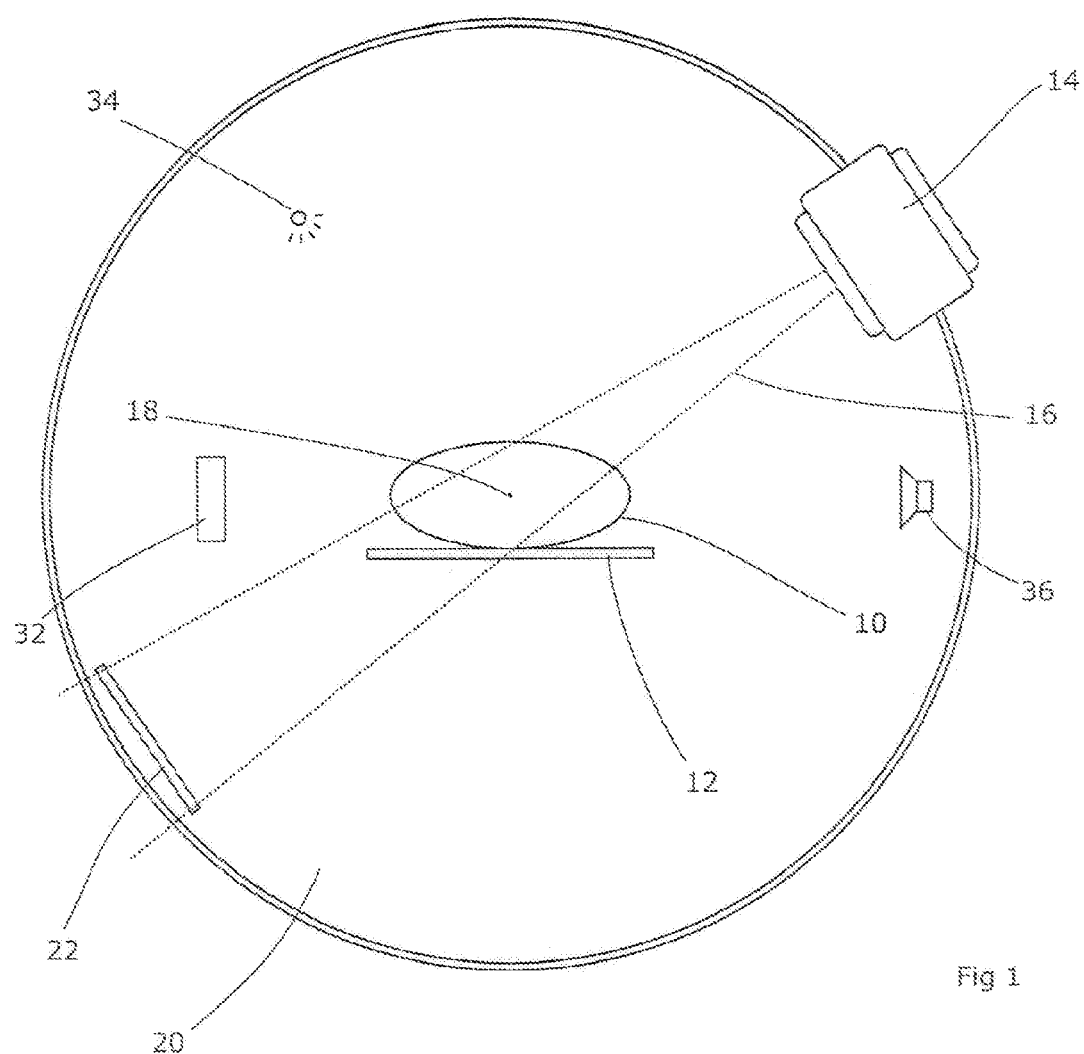
FIG. 1 is a view of a cone beam CT scanner according to the present invention, viewed along the axis of rotation thereof.

FIG. 1 shows a cone beam CT scanner. A patient 10 is supported on a couch 12 which may be of any suitable design. Couches typically allow the elevation and longitudinal position of the patient to be adjusted and this may be provided for as desired. An x-ray source 14 is arranged to project a wide beam 16 of radiation generally directed towards the isocentre 18 of the patient. The source 14 is rotatable around the isocentre 18 on a rotational support 20. The support can, for example, be in the form of a ring or annulus around the patient 10 and couch 12 in which the source is mounted, or it can be a C-arm, or any suitable support allowing the source to rotate, or any combination thereof. A two-dimensional flat-panel detector 22 is also mounted on the support 20, opposite the source 14 and arranged to rotate in synchronism therewith. If the support includes a C-arm then this can be achieved by mounting the detector on the opposite arm.

Figure 2:
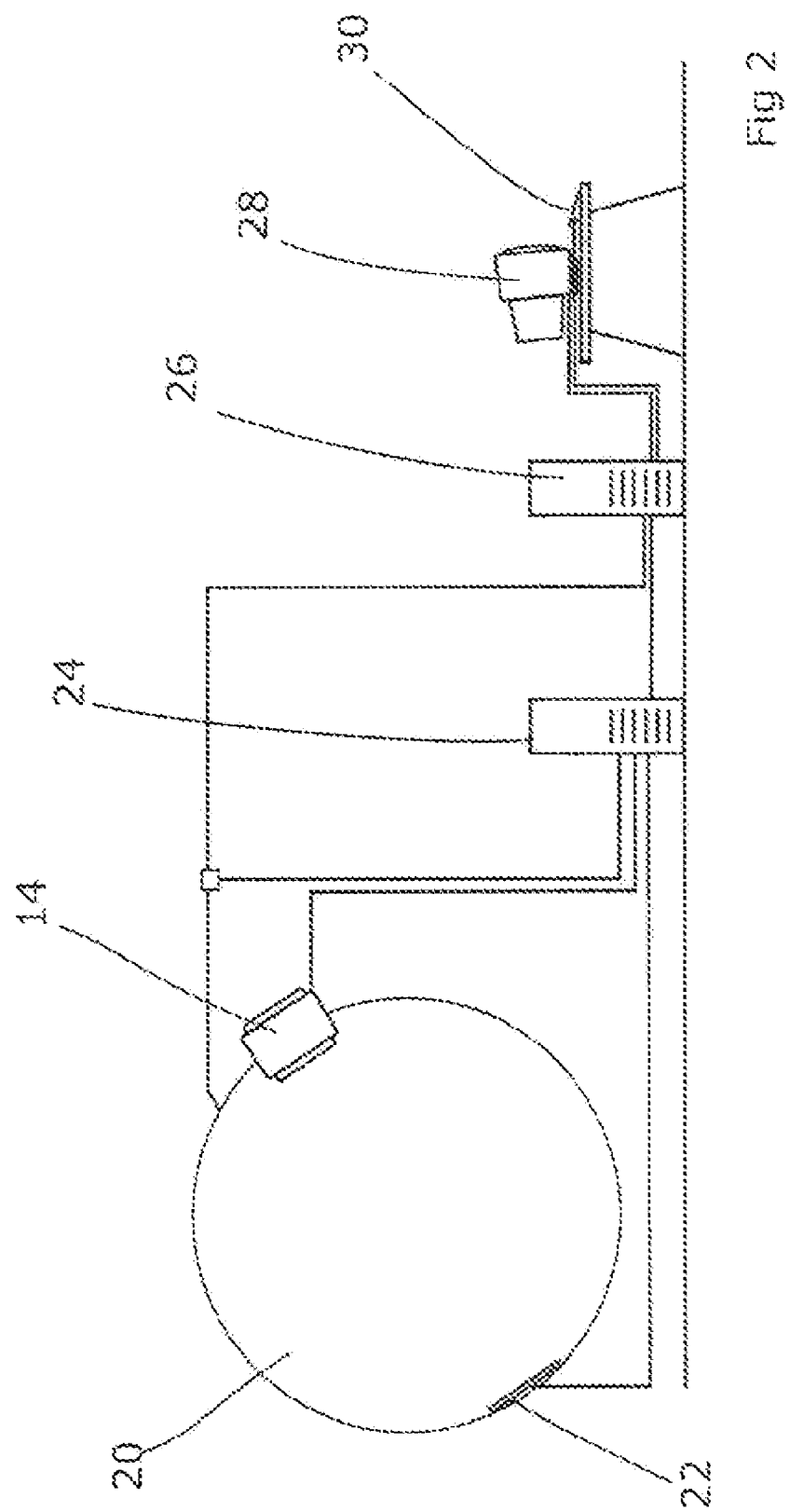
FIG. 2 is a schematic view of the system incorporating such a scanner.

Thus, radiation emitted by the source 14 is partially absorbed by the patient and the attenuated signal is detected by the flat panel detector 22. The source 14 and detector 22 are then indexed rotationally and a fresh image obtained. This is repeated until sufficient images are acquired to reconstruct the volume data, typically one complete rotation. FIG. 2 shows the system as a whole. The scanner of FIG. 1 is shown, together with cables linking the source 14, detector 22 and rotational support 20 to a plurality of computing means 24, 26 which process the data generated including the images, source intensity (etc), and rotational support position. Data is output via any suitable means, depicted generally as a monitor 28 but not limited thereto, and the system is controlled by any suitable input means, again depicted generally as a keyboard 30 but likewise not especially limited thereto.

As mentioned above, we have found that there are artifacts in the reconstructed volume data of cone beam CT systems, which we have traced to patient breathing movements. To overcome or alleviate these, respiration correlation techniques are applied to the acquired projection images by the computing means 24, 26. This differs from conventional respiration-correlated CT scanning in acting on the acquired projection images rather than the reconstructed CT volume.

To assist in this process, a breath control system is provided at 32 to monitor the phase of the patients breathing while the projection images are acquired. On completion of the acquisition, projection images that have comparable breathing phases can be selected from the complete set, and these are used to reconstruct the volume data using cone beam CT techniques. As a result, any phase or range of phases can be selected and therefore the effect of breathing can be studied if desired.

As an alternative to the breath control system, it is possible to use a feature in the projection image(s) to determine the breathing phase, such as the position of the patient's diaphragm. This cain then be used to select the relevant images to be used in the projection process.

An alert system including a light 34 and a buzzer 36 is provided, to prompt the patient visually and audibly in order to ensure a regular amplitude and pattern of breathing. Other alerts could of course be employed, such as other forms of visible prompts including (for example) movable devices, and other forms of audible prompts including (for example) speakers, percussive devices or any other form of controllable sound generation apparatus.

Figure 3:
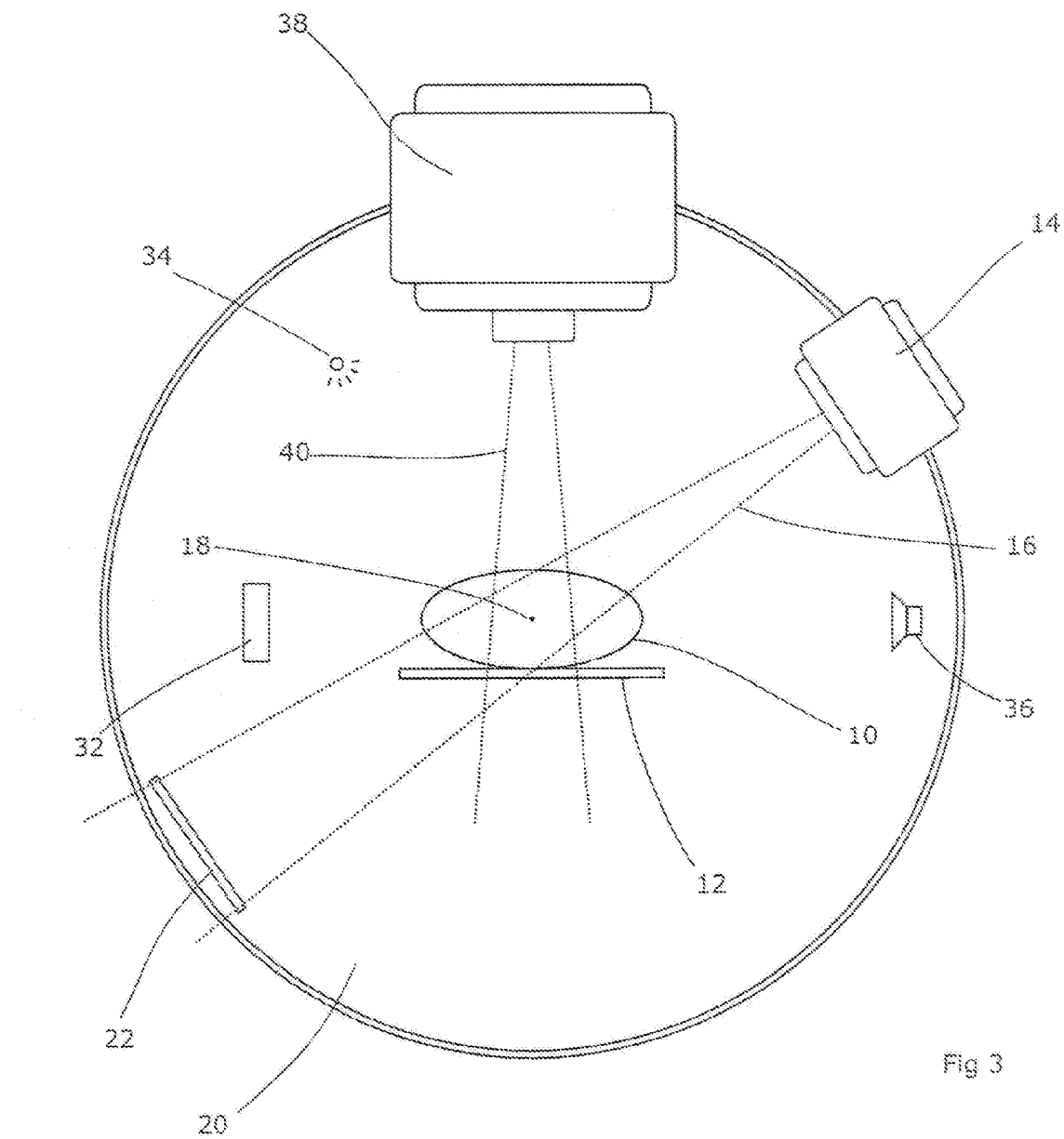
FIG. 3 shows a treatment apparatus including the scanner of the present invention.

FIG. 3 shows a system including a therapeutic source of radiation 38 arranged to emit a suitably collimated beam of therapeutic radiation 40. This allows simultaneous scanning and treatment. If the radiation from source 14 continues during the treatment the selected feature (above) in the projection images can be used to control delivery of therapeutic radiation form the source 38, dependent on the patient's breathing cycle. This ensures that the tumor is in the correct position when the radiation is delivered. This will provide a direct measure of the patient's breathing phase, a significant improvement as compared to current methods that use external markers affixed to the patient. The use of the same direct measure of the patient's breathing phase and patient position to generate the 3D volume data set and control the treatment delivery will remove significant uncertainties.

It will of course be understood that many variations may be made to the above-described embodiment without departing from the scope of the present invention.

What is claimed is:

1. A method of cone beam CT scanning, the method comprising:

performing cone beam CT scanning to acquire two-dimensional projection images of a patient;

for each of a plurality of projection images, using a feature within the projection image to determine breathing phase for that projection image; and applying respiration correlation techniques directly to the projection images based on the determined breathing phase.

2. A method of cone beam CT scanning according to claim 1 in which projection images that have comparable breathing phases are selected from the complete data set on completion of the acquisition and are used to reconstruct the volume data.

3. A method of cone beam CT scanning according to claim 1 in which the feature is the position of the patient's diaphragm.

4. A method of cone beam CT scanning according to claim 1 in which visual and/or audible prompts are provided for the patient's breathing.

5. A method of cone beam CT scanning according to claim 1 in which therapeutic radiation is delivered during the scan at times correlated with the patient's breathing cycle.

6. A cone beam CT scanner comprising:

means for performing cone beam CT scanning to acquire two-dimensional projection images of a patient;

means for using a feature within the projection image for each of a plurality of projection images to determine breathing phase for that projection image; and means for applying respiration correlation techniques directly to the projection images based on the determined breathing phase.

7. A cone beam CT scanner according to claim 6 arranged to select projection images that have comparable breathing phases from the complete data set on completion of the acquisition and to use these to reconstruct the volume data.

8. A cone beam CT scanner according to claim 6 in which the feature is the position of the patient's diaphragm.

9. A cone beam CT scanner according to claim 6 including means to provide visual and/or audible prompts for the patient's breathing.

10. A radiotherapy device comprising a cone beam CT scanner and a source of therapeutic radiation, wherein the CT scanner:

performs cone beam CT scanning to acquire two-dimensional projection images of a patient;

uses a feature within the projection image for each of a plurality of projection images to determine breathing phase for that projection image; and applies respiration correlation techniques directly to the projection images based on the determined breathing phase to deliver therapeutic radiation during the scan.

\* \* \* \* \*